United States Patent
Paolo et al.

(10) Patent No.: US 9,861,528 B2
(45) Date of Patent: Jan. 9, 2018

(54) SKI GOGGLES WITH MEANS FOR ADJUSTING THE FIT OF THE NASAL SUPPORT REGION

(75) Inventors: Guadagnin Paolo, Pederobba (IT); Benvegnu' Ivo, Padua (IT)

(73) Assignee: SAFILO SOCIETA'AZIONARIA FABBRICA ITALIANA LAVORAZIONE OCCHIALI S.P.A., Pederobba (TV) (IT)

(*) Notice: Subject to any disclaimer, the term of this patent is extended or adjusted under 35 U.S.C. 154(b) by 350 days.

(21) Appl. No.: 14/361,105

(22) PCT Filed: Nov. 28, 2011

(86) PCT No.: PCT/IB2011/055339
§ 371 (c)(1),
(2), (4) Date: May 28, 2014

(87) PCT Pub. No.: WO2013/079990
PCT Pub. Date: Jun. 6, 2013

(65) Prior Publication Data
US 2014/0331394 A1 Nov. 13, 2014

(51) Int. Cl.
*A61F 9/02* (2006.01)
*A42B 3/18* (2006.01)
(Continued)

(52) U.S. Cl.
CPC .......... *A61F 9/02* (2013.01); *A61F 9/026* (2013.01); *A61F 9/027* (2013.01); *A61F 9/029* (2013.01)

(58) Field of Classification Search
CPC ............. A61F 9/02; A61F 9/026; A61F 9/027
(Continued)

(56) References Cited

U.S. PATENT DOCUMENTS

| 666,927 A | * | 1/1901 | Finch ................ G02C 5/12 |
| | | | 2/446 |
| RE13,231 E | * | 5/1911 | Cook ................ 2/446 |

(Continued)

FOREIGN PATENT DOCUMENTS

| WO | 2011082718 A1 | 7/2011 |
| WO | WO2011082719 | * 7/2011 |

OTHER PUBLICATIONS

ISR and Written Opinion dated Apr. 3, 2012 in corresponding PCT application PCT/IB2011/055339.

*Primary Examiner* — Clinton T Ostrup
*Assistant Examiner* — Cameron A Carter
(74) *Attorney, Agent, or Firm* — Kristina Castellano; Castellano PLLC

(57) ABSTRACT

A protective mask for sports use that includes a front frame for the retention of at least one lens, a nasal support element, the fit of the nasal support element being adjusted, by adaptation of the frame to the shape of the face in the nasal support region. The support element is structurally independent of the front frame and at least one appendage is mounted to be rotatable on the front frame, at the nasal support region, about an axis of rotation and also acting on the nasal support element, in order to displace the support relative to the front frame, the at least one appendage being reversibly locked in a selected angular position relative to the frame, about the axis, so as to improve the adaptation of the nasal support element to the shape of the nasal region of the face.

10 Claims, 4 Drawing Sheets

(51) Int. Cl.
 *A42B 3/22* (2006.01)
 *A41D 13/00* (2006.01)
 *A42B 1/00* (2006.01)

(58) Field of Classification Search
 USPC ..................................... 2/439, 6.3, 426, 446
 See application file for complete search history.

(56) References Cited

U.S. PATENT DOCUMENTS

| | | | | |
|---|---|---|---|---|
| 1,923,566 | A | * | 8/1933 | Baker ..................... A61F 9/026 2/445 |
| 1,960,451 | A | * | 5/1934 | Pappert .................... G02C 5/02 351/140 |
| 6,106,117 | A | * | 8/2000 | Huang Lin ............ G02C 5/122 351/136 |
| 7,318,437 | B2 | * | 1/2008 | Gunaratnam ..... A61M 16/0666 128/206.11 |
| 9,642,749 | B2 | * | 5/2017 | McNeal .................. A61F 9/026 |
| 2007/0024806 | A1 | * | 2/2007 | Blanshay ................ G02C 9/00 351/62 |
| 2007/0277297 | A1 | * | 12/2007 | Chiang ............... A63B 33/002 2/426 |
| 2009/0038060 | A1 | * | 2/2009 | Chiang ............... A63B 33/002 2/440 |
| 2010/0220283 | A1 | * | 9/2010 | Pulito .................... A61F 9/026 351/62 |
| 2010/0225879 | A1 | * | 9/2010 | Pulito .................... A61F 9/026 351/137 |
| 2011/0265254 | A1 | * | 11/2011 | Ma ........................ A61H 7/006 2/420 |

* cited by examiner

SKI GOGGLES WITH MEANS FOR ADJUSTING THE FIT OF THE NASAL SUPPORT REGION

CLAIM FOR PRIORITY

This application is a U.S. National Stage Application of PCT/IB2011/055339 filed on Nov. 28, 2011, the contents of which are hereby incorporated herein by reference.

TECHNICAL FIELD

The present invention concerns a protective mask for sports use, in particular for skiing disciplines, having the features mentioned in the preamble of main claim No. 1.

TECHNOLOGICAL BACKGROUND

In the technical field of reference, protective masks for sports use, and in particular those intended for use in skiing disciplines (skiing, snowboarding, etc), typically comprise a front frame for the retention of a lens, and which is provided with a gasket element extending along the perimetral profile of the frame and intended to ensure a seal when the mask is in contact on the face. Bearing with effective contact along the entire profile of the frame is desirable both for a comfortable fit on the face and for the function of sealing and protection which must be ensured during the sporting activity. Typically, the same mask is intended to be fitted onto facial morphologies which obviously differ from one another, thus seeking to arrive at a state of best compromise in the adaptability to different facial shapes. However, ensuring an optimum fit becomes problematic in the nasal support region of the mask, by reason of the differences in morphology and curvature that may be encountered, even in a very accentuated form, but still located in an area of limited width (that involved in the nasal region), and therefore difficult to compensate in the supporting of the mask on the nasal region.

DESCRIPTION OF THE INVENTION

The principal aim of the present invention is that of providing a protective mask for sports use, and in particular for skiing disciplines, which is structurally and functionally designed to remedy the limitations indicated above with reference to the prior art, in order to improve the adaptation of the fit of the mask on the nasal region of the face.

These and other aims which will become clear hereinafter are achieved by a protective mask for sports use, in particular for skiing disciplines, produced in accordance with the attached claims.

BRIEF DESCRIPTION OF THE DRAWINGS

Further features and advantages of the invention will become clearer from the following detailed description of a preferred exemplary embodiment thereof, illustrated by way of non-limiting example with reference to the appended drawings, in which.

PREFERRED EMBODIMENT OF THE INVENTION

Figure 1:
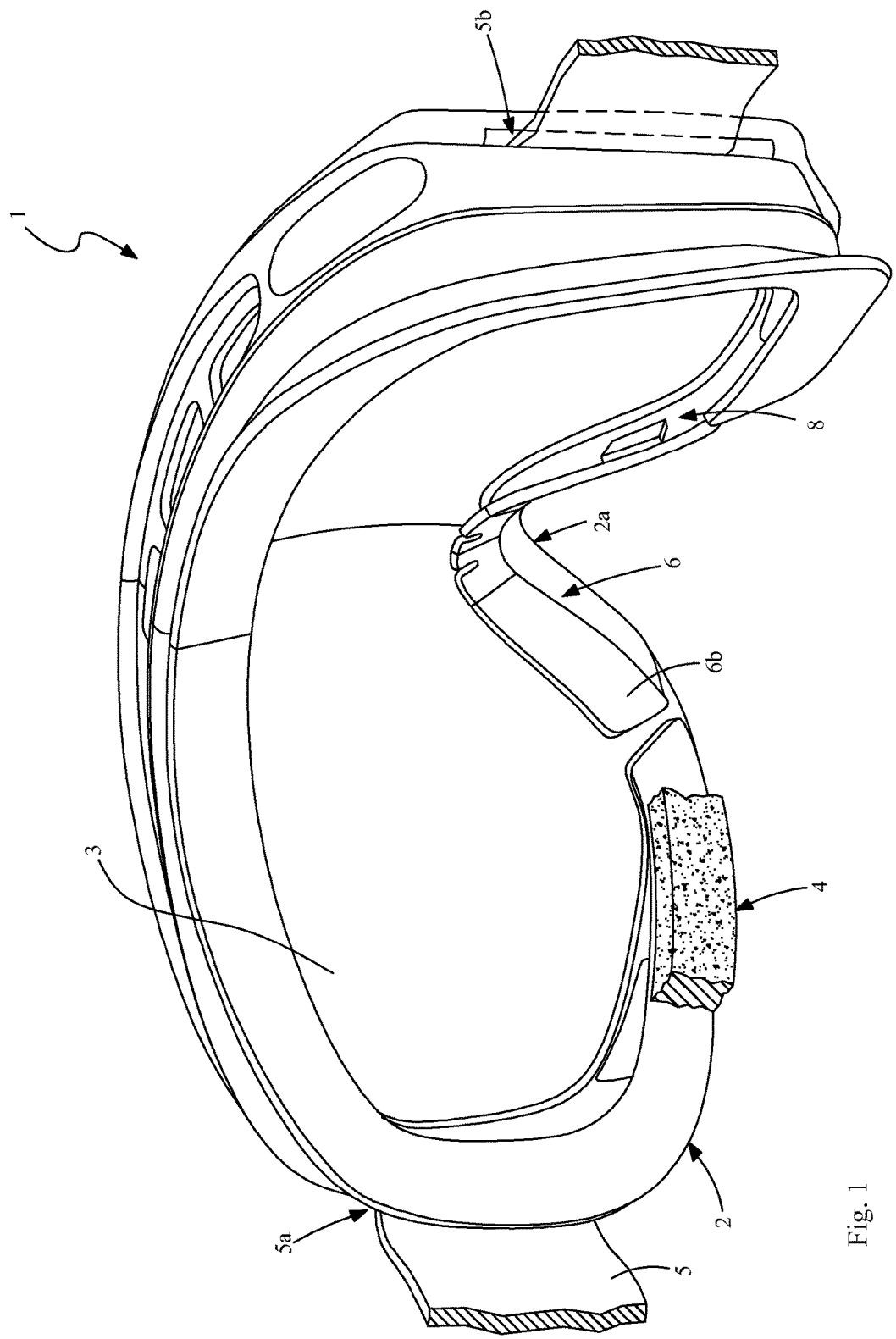
FIG. 1 is a partial perspective view of a mask for sports use produced according to the present invention.
Figure 2:
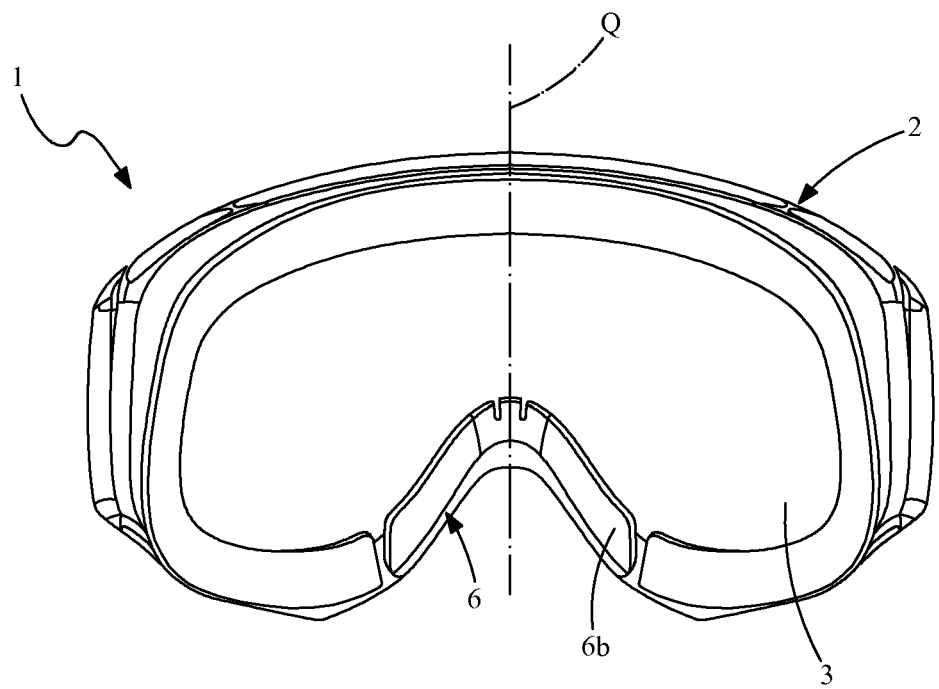
FIG. 2 is a front view of a detail of the mask of FIG. 1.
Figure 3:
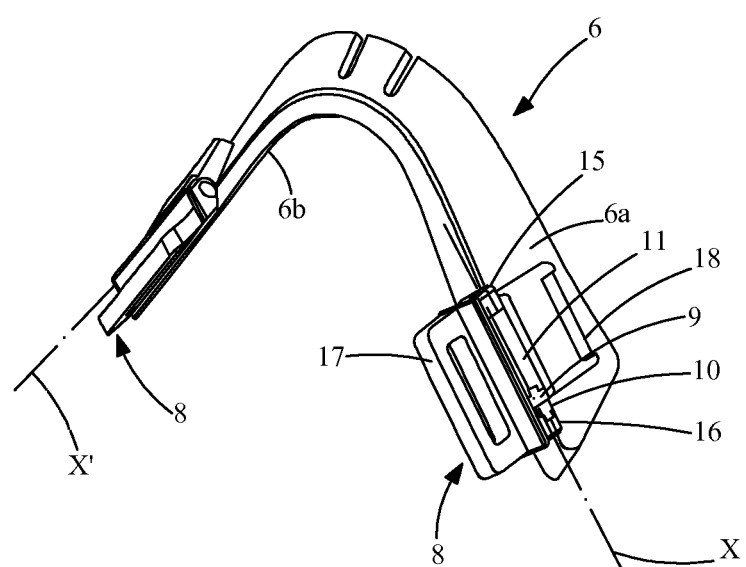
FIG. 3 is a perspective view on an enlarged scale of a detail of the mask of the preceding figures.
Figure 4:
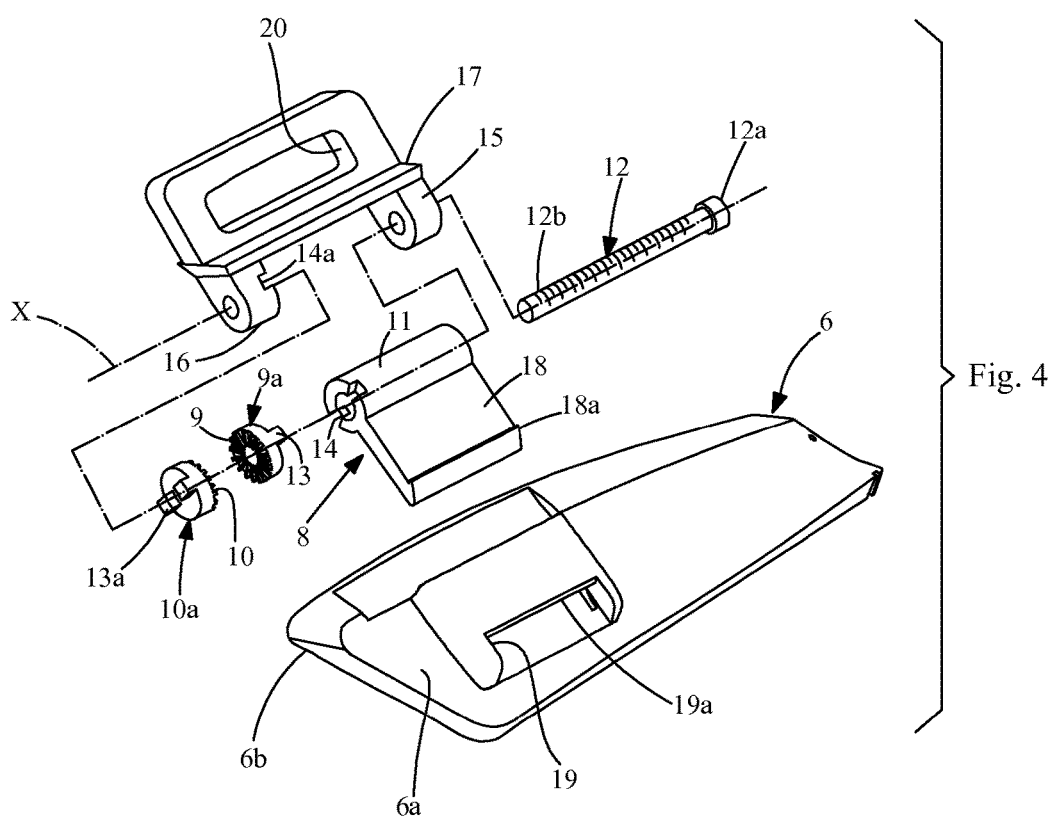
FIG. 4 is an exploded perspective view of a part of the detail of FIG. 3.
Figure 5:
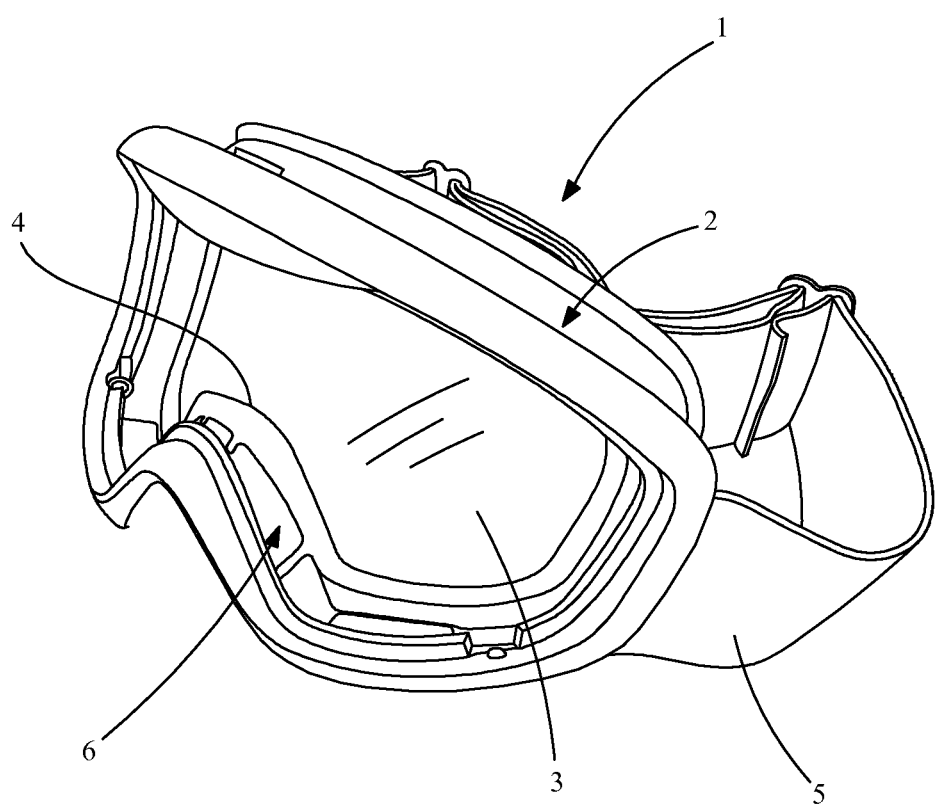
FIG. 5 is a perspective view of the mask of the preceding figures.

With reference to the drawings listed, the reference 1 indicates as a whole a protective mask for skiing disciplines (skiing, snowboarding, etc) produced according to the present invention.

The mask 1 comprises a front frame 2 of conventional type for the retention of a lens 3 and is provided with a gasket element 4 extending along the perimetral profile of the frame and which is intended to ensure a seal when the mask is in contact on the face. The mask 1 is also provided with a resilient strap, indicated by 5, having respective ends 5a, 5b secured to respective laterally opposed portions of the front frame. A mechanism for adjusting the length and consequent tensioning of the resilient strap, of conventional type per se, is provided on the resilient strap 5. The mask further comprises a nasal support and bearing element, indicated by 6, which is structurally independent of the frame 2 and extends at the nasal region of the face and is also intended, together with the portion of gasket 4 associated therewith, for the support, with bearing contact, of the mask in said nasal region when the mask is worn on the face.

According to a principal feature of the invention, the mask 1 is provided with means for adjusting the fit of the nasal support element 6 on the nasal region, by adjusting the adaptation of the support element to the shape of the face in the aforesaid nasal region. Said means comprise a pair of appendages, both indicated by 8, mounted to be rotatable on a frame portion 2a extending in the region of the nasal support element 6, about respective axes of rotation (X, X'), in the nasal support region, and also extending on opposite sides of said frame portion 2a with respect to a central median plane of symmetry of the mask, indicated by Q in the drawings, passing through the nasal support region of the mask.

The appendages 8, although they are designed with a symmetrical mirror-image structure relative to the plane Q, as can be seen from the drawings, are intended to perform the same function in the respective nasal support regions, therefore only one of the appendages 8 will be described in detail hereinafter, the description being substantially applicable also to the other, opposite, appendage.

Each appendage 8 acts on the nasal support element 6 and can also be reversibly locked in a selected angular position relative to the front frame 2, about the axis of articulation X, so as to adapt as far as possible the profile of the support element 6 to the configuration of the nasal region of the face, in this way adjusting the fit in dependence on the corresponding profile and the dimension of the nasal region itself.

The appendage 8 acts on a portion of the nasal support element 6, as will be explained in more detail in the continuation of the description, and is capable of being oriented, by means of rotation about the corresponding axis X, into a selected angular position relative to the frame, reversible locking means being provided between the frame 2 and each appendage 8, for the purpose of modifying, owing to its flexibility, the profile of the portion of nasal support element 6, selecting the best adaptation between the element and the surface of the nasal region on which the bearing contact extends.

For the function of adjustment and locking of the appendages 8, for each of said appendages, means are provided which comprise a first and a second set of teeth 9, 10 having a frontal toothed profile and extending concentric with the respective axis of rotation X (X'). The sets of teeth 9, 10, are capable of frontal meshing with each other and are solidly secured respectively to the frame 2 and to the corresponding appendage 8 so that, to a state of meshing between the sets of teeth 9, 10, there corresponds a respective relative angular positioning between the frame 2 and the corresponding appendage 8, such positioning being adjustable as a result of the relative rotation between the sets of teeth meshing with each other.

More particularly, the sets of teeth 9, 10 are provided on respective disc-shaped bodies 9a, 10a, which can be mounted coaxially with the corresponding axis of rotation X and can also be reversibly secured to the corresponding appendage 8 and the frame 2, respectively. Provided in the appendage 8 is a tubular portion 11 suitable for being slipped coaxially onto a pin 12 for articulation of the appendage, about the corresponding axis X (X'), there being mounted at one end of said portion the disc-shaped body 9a, which is also hollow centrally so as to be slipped coaxially onto the pin 12. Between the body 9a and the tubular portion 11 a rotational locking is provided by form-fit coupling between a projection 13 and a respective seat 14 for the projection, which are provided respectively on the disc-shaped body 9a and on the tubular portion 11.

Preferably, the protuberance 13 and the corresponding seat 14 extend in a diametrical direction with respect to the axis of articulation.

The references 15, 16 indicate a pair of supports rising in the same direction from a base 17 for attachment to the frame, between which the pin 12 is secured. The pin is conveniently provided in the form of a screw with a head 12a and a threaded portion 12b, and is arranged to pass through a pair of holes coaxial with each other and with the articulation axis X of the pin, so that the head 12a is abutted by one (15) of the supports and the threaded portion 12b is screwed into the hole provided on the other (16) of the supports.

The disc-shaped body 10a, which is also hollow centrally, can be locked rotationally to the support 16, by means of a similar form-fit coupling between a projection 13a and a respective seat 14a for the projection, which are respectively provided on the disc-shaped body 10a and on the support 16 adjacent thereto.

The reference 18 indicates a plate-like part of the appendage 8 adjacent to the tubular portion 11.

By means of the configuration described above, the disc-shaped bodies 9a, 10a are axially aligned, coaxially with the axis of rotation X, between the supports 15, 16.

The axial coupling clearances between the supports 15, 16, the disc-shaped bodies 9a, 10a, and said tubular portion 11, in combination with the resilient yielding of the materials from which they are obtained, provide a "snap" type rotation mechanism, between the toothed profiles of the sets of teeth 9, 10 meshing with each other, in the passage between consecutive angular positions, during which the toothed profile of one set of teeth (9) slides on the toothed profile of the other (10) between one meshing state and the next, until the selected relative angular orientation between the frame 2 and the corresponding appendage 8 is reached.

The plate-like part 18 of each appendage 8 can be coupled in a form-fit in a seat 19 arranged on a surface 6a of the nasal support element, the relative locking being effected by means of a tooth-like formation 18a provided at the free end of the plate-like part 18, which can abut against a surface abutment 19a of the seat 19, so as to ensure the retention of the part 18 in the seat 19.

The nasal support element 6 has a curved profile and is made of a resiliently yielding material as a slim body defined between the surface 6a, against which the appendages 8 act, and an opposed surface 6b, which is intended for fixing with the gasket 4. The gasket therefore extends in extension of the perimetral profile of the frame 4 on which the gasket presses. Owing to the marked yielding of the sealing gasket, the latter easily follows the deformation of the nasal support element 6, assuming the corresponding curvature thereof produced by the action of the appendages 8.

Alternatively, it is possible to make the support element 6 of a material which is yielding and has a degree of softness equivalent to that of the gasket 4, so that to the support element there is not fixed a portion of the gasket extending along the profile of the frame, but it is the nasal support element itself which ensures adequate comfort and sealing in the bearing contact with the nasal region.

In order to secure the attachment base 17 to the frame 2, it is possible to provide a respective slot 20 passing through the base itself, intended to be engaged, by means of a resilient form-fit coupling, by a hook type formation, not shown, provided in the frame 2.

In one variant it is possible to provide for the insertion of the attachment bases 17 into the injection mould for the frame 2, in which case the slot 20 of the base contributes to the gripping of the material of the frame 2 on the appendage 8.

The invention thus achieves the aims proposed, providing numerous advantages compared with known solutions.

A principal advantage is linked to the fact that, owing to the mechanism for snap-type adjustment of the fit of the mask in the nasal region, it is possible to obtain, with the same mask, the best adaptation of fit even in the case of different facial morphologies in the nasal support region, ensuring the most homogeneous and continuous bearing contact of the mask in the whole of the nasal region, improving the comfort of the fit as well as the sealing function (in surface contact) of the mask.

Owing to the fact that for each state of relative meshing of the sets of teeth of the snap mechanism there corresponds a different profile and curvature of the nasal support element, the precision in the adjustment of the fit is also improved, ensuring adequate comfort and sealing even in the presence of reduced morphological variations of the nasal support region of the mask.

The invention claimed is:

1. A sports protective mask, comprising: a front frame for retention of at least one lens, a nasal support element extending along a perimetral profile of the frame at a nasal region and also capable of surrounding the nasal region with bearing contact when the mask is worn on a face, and an adjustment mechanism for adjusting fit of the nasal support element, by adaptation of the frame to the shape of the face in the nasal region, wherein said nasal support element is structurally independent of the front frame and is removable from the front frame, and wherein said adjustment mechanism comprises at least one appendage mounted to be rotatable on the front frame, at the nasal region, about an axis of rotation (X; X') and also acting on the nasal support element, in order to rotate the nasal support element in relation to the front frame, and a locking mechanism for reversible locking of said at least one appendage in a selected angular position relative to the frame, about said axis, so as to improve the adaptation of the nasal support element to the shape of the nasal region of the face; wherein each appendage comprises a tubular portion suitable for being slipped coaxially onto a pin for articulation of the appendage about said axis, for the rotatable mounting of the appendage with respect to the frame, the articulation pin being secured between a pair of support rising from a base for attachment to the frame, a first disc-shaped body being mounted on one of the supports in a position opposite said first body, so that the tubular portion, the first and a second disc-shaped body, are axially aligned, coaxially with the axis of rotation, between said supports; wherein adjustment and locking mechanisms comprise a first and second set of teeth having a frontal toothed profile, the first and second sets of teeth being able to mesh with each other; wherein the first and second sets of frontal teeth are provided on the respective first and second disc-shaped body; and wherein axial coupling between the supports and the disc-shaped bodies and also the tubular portion, provide rotation between the toothed profiles of the sets of teeth in relative meshing, in the passage between consecutive angular positions, during which the toothed profile of one set of teeth slides on the toothed profile of the other between one state of meshing and the next, until the selected relative angular orientation between the frame and the corresponding appendage is reached.

2. The mask according to claim 1, wherein a pair of appendages are provided, extending on opposite sides of the frame with respect to a central median plane of symmetry of the mask, passing through the nasal region of the mask.

3. The mask according to claim 2, wherein the frontal toothed profile is concentric with the axis of rotation (X; X'), the first and second sets of teeth being solidly secured respectively to the corresponding appendage and to the frame, so that to a state of mutual meshing between the sets of teeth there corresponds a respective relative angular positioning between the frame and the corresponding appendage, said relative positioning being adjustable as a result of the relative rotation between the sets of teeth meshing with each other.

4. The mask according to claim 3, wherein the disc-shaped bodies can be mounted coaxially with said axis, and can also be reversibly secured, respectively, to the corresponding appendage and to the frame.

5. The mask according to claim 1, wherein the axial coupling clearances between the supports and the disc-shaped bodies and also the tubular portion, in combination with the resilient yielding of the materials from which they are obtained, provide a snap-type rotation mechanism.

6. The mask according to claim 1, wherein the articulation pin passes through the supports and can be clamped on the supports by screw clamping.

7. The mask according to claim 6, wherein the pin is provided in the form of a screw with a head abutted by one of the supports and with a threaded portion that can be screwed into the other of said supports.

8. The mask according to claim 7, wherein each appendage comprises a plate part adjoining the tubular portion, the plate part being capable of form-fit coupling in a respective seat arranged in the nasal support element.

9. The mask according to claim 8, comprising a gasket element extending continuously along the perimetral profile of the frame and also in the region of the nasal support element, on the opposite side from said seats for securing the appendages, so as to ensure a seal in the area of contact on the face, along the entire perimetral profile of the frame as well as in the region of the nasal support element.

10. The sports protective mask of claim 1, wherein the mask is a ski mask.

* * * * *